(12) United States Patent
Hart et al.

(10) Patent No.: US 9,340,839 B2
(45) Date of Patent: May 17, 2016

(54) INTEGRATED TEMPERATURE CONTROL OF LABORATORY INSTRUMENT

(71) Applicants: Brendan Hart, Troy, NY (US); Brian Kolb, Averill Park, NY (US); David Grinnell, Averill Park, NY (US); Ian Glasgow, Averill Park, NY (US)

(72) Inventors: Brendan Hart, Troy, NY (US); Brian Kolb, Averill Park, NY (US); David Grinnell, Averill Park, NY (US); Ian Glasgow, Averill Park, NY (US)

(73) Assignee: Forward Biotech, Inc., Averill Park, NY (US)

(*) Notice: Subject to any disclaimer, the term of this patent is extended or adjusted under 35 U.S.C. 154(b) by 0 days.

(21) Appl. No.: 14/245,530

(22) Filed: Apr. 4, 2014

(65) Prior Publication Data

US 2014/0302485 A1    Oct. 9, 2014

Related U.S. Application Data

(60) Provisional application No. 61/808,255, filed on Apr. 4, 2013.

(51) Int. Cl.
*C12Q 3/00* (2006.01)
*G01N 1/28* (2006.01)
*B01L 7/00* (2006.01)

(52) U.S. Cl.
CPC ... *C12Q 3/00* (2013.01); *B01L 7/50* (2013.01); *B01L 7/52* (2013.01); *B01L 2200/147* (2013.01); *B01L 2300/1844* (2013.01); *B01L 2300/1894* (2013.01); *G01N 2001/2866* (2013.01); *Y10T 436/12* (2015.01)

(58) Field of Classification Search
CPC ....... B01L 7/00; B01L 7/02; B01L 2200/147; B01L 2300/1844; B01L 2300/1894; B01L 7/50; B01L 7/52; C12Q 3/00; Y10T 137/1963; G01N 2001/2866
USPC .......................................... 422/561, 567, 943
See application file for complete search history.

(56) References Cited

U.S. PATENT DOCUMENTS

| | | | |
|---|---|---|---|
| 3,380,499 A | | 4/1968 | Vocci et al. |
| 5,567,050 A | * | 10/1996 | Zlobinsky et al. ............ 366/209 |
| 5,577,837 A | | 11/1996 | Martin et al. |
| 5,709,104 A | * | 1/1998 | Howcroft ..................... 62/457.1 |
| 5,769,538 A | * | 6/1998 | Sherman et al. ............. 366/198 |
| 6,209,343 B1 | * | 4/2001 | Owen .......................... 62/457.2 |
| 7,785,868 B2 | | 8/2010 | Yuan et al. |
| 2006/0053828 A1 | * | 3/2006 | Shallman et al. ............ 62/457.9 |

FOREIGN PATENT DOCUMENTS

EP    2644690 A1    10/2013

* cited by examiner

*Primary Examiner* — Dennis M White
*Assistant Examiner* — Bryan Kilpatrick

(57) ABSTRACT

This invention describes an advanced cooling system for a laboratory instrument to maintain laboratory samples at a predetermined temperature. The advanced cooling system uses an algorithm that incorporates information from at least one sensor and other operational parameters including thermal effects from the operation of the instrument.

18 Claims, 2 Drawing Sheets

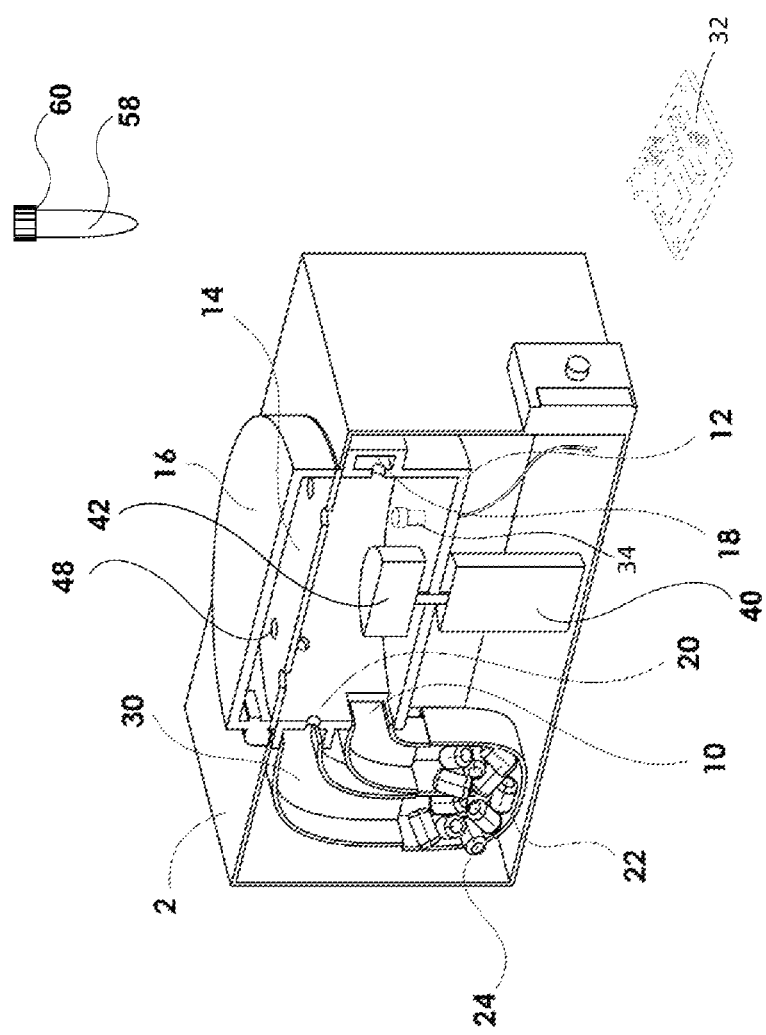

INTEGRATED TEMPERATURE CONTROL OF LABORATORY INSTRUMENT

FIELD OF THE INVENTION

The invention herein pertains to the temperature control system of a laboratory instrument.

BACKGROUND OF THE INVENTION

This invention applies to instruments that process biological and chemical samples. Many samples, particularly biological samples degrade if they heat up. Likewise, they can degrade if they freeze. With this in mind, it is often important to keep samples near 4° C. Therefore, a good method to accurately control the temperature of samples within a few degrees is needed. This invention provides such a method.

One common application is homogenization, the dissociation and disruption of cells and tissues to release nucleotides, proteins, virus, molecules, chemicals, or whole cells for scientific analysis. During homogenization, biological samples typically heat up and degrade, unless the process is paused and samples are permitted to cool. Heating of a sample is undesirable, as is pausing during homogenization to allow a sample to cool before proceeding further. It is often desirable to disrupt multiple samples simultaneously in individual tubes or containers to avoid cross contamination and to save time. A striking technology has been described to mechanically disrupt substances in tubes (U.S. Pat. No. 5,769,538 to Sherman). This technology is based on strikers that rotate around a hub or an axis and rapidly contact the tubes with contents inside. The impact of the strikers on the tubes induces turbulent motion of the contents, resulting in mixing, re-suspension, homogenization or disruption of the tube contents. Advantages of the current invention are maintenance of the sample at a specific temperature and maintenance of the reagents at a specific temperature.

SUMMARY OF THE INVENTION

In view of the shortcomings of the existing technology, this invention provides a method of temperature control for laboratory samples in a laboratory instrument by providing forced convection with a flow of air by a thermal mass. The amount of cooling is modulated by the electronic circuit which also controls the operation of the instrument.

DESCRIPTION OF THE FIGURES

In FIG. 2, a cross section of the chamber of the instrument, the electronic circuit (32) also controls the motor (40) and monitors the sensor (34). Inside the sample chamber (12), the cold air passes by the sample tubes (58). Heat from the samples inside the sample tubes (58) passes through the sample tube walls and is transferred to the cold air. The holder of the sample tubes (14) contains holes (48) for holding the sample tubes (58). The sample tubes (58) fit loosely in the holes, so they are free to oscillate rotationally about axes in the lateral plane and linearly in the vertical direction. The shoulder of the tube sleeves (56) in FIG. 1, or the base of the cap (60) or the lip of the sample tubes (58) prevents them from falling through the holder of the sample tubes (14). The pellets (24), such as dry ice pellets, cold packs, or similarly cold objects or thermal transfer device, are located in the bucket (22). There is an inlet (10) to the bucket (22). The air exits the bucket (22) and enters a channel (18) with a series of ports (20) that lead into the sample chamber (12) with a lid (16) and a holder of the sample tubes (14). The ports (20) enable the cold air to be evenly dispersed into the sample chamber (12). One or more sensors (34) can be located in the instrument. The sensors (34) monitor the motor, the samples tubes (58), or the temperature in the sample chamber (12). A valve which could be located at the outlet (30) of the bucket (22), diverts air from the channel (18), thereby modulating how much cold air flows into the channel (18).

DESCRIPTION

Figure 1:
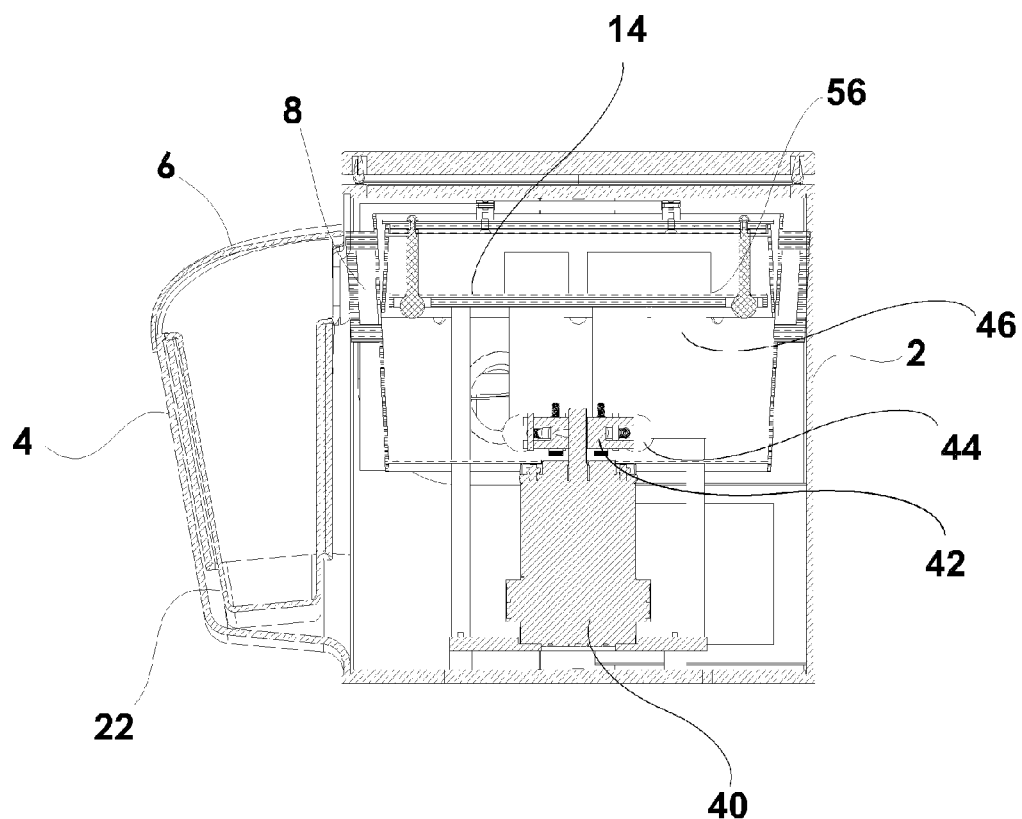
In FIG. 1, a cross section of the instrument, item (2) represents the homogenizer instrument. Motor (40) rotates a hub (42). Strikers (44) independently pivot from the hub (42). As the motor (40) rotates the hub (42), the strikers (44) swing into and impact the tube sleeves (46). The tube sleeves (46) fit in holes in the holder of the sample tubes (14), and hold the sample tubes (58) which hold the samples. In this way, the instrument can use sleeve type sample holders in addition to tube type sample holders. The shoulder (56) on the tube sleeves (46) prevent the tube sleeves (46) from falling through the holder of the sample tubes (14). These impacts cause the tube sleeves (46) to oscillate vigorously. Alternatively, as described in the background section, the tube sleeves (46) are not present and the strikers (44) can impact the sample tubes (58) directly. The housing has a region (4) for containing a bucket (22) to hold a cold thermal mass, such as dry ice, cold packs or other cold substance. The lid of the region (6) helps thermally insulate the bucket (22). A fan (8) in the path of the air flow, is modulated to control the air flow. Air flows across or through the bucket (22), as well as the porous thermal mass shown in FIG. 2, such as pellets (24), which are significantly colder than the ambient air, and the sample tubes (58). The means for forcing air by the cold thermal mass includes the fan (8). The means for modulating the air flow includes an electronic circuit (32) pictured in FIG. 2 to modulate the fan (8).

The current invention allows maintenance of samples and reagents at a specific temperature. The invention is a laboratory instrument that contains an integrated cooling system and homogenizes samples by using a motor to rotate a hub with pivoting strikers. As the motor rotates the hub, the strikers swing radially outward from the axis of rotation of the hub, and impact the sample holders. As indicated in the background section, the strikers can hit the sample tubes, or as shown in FIG. 1, the strikers can hit the tube sleeves in which the sample tubes are placed, causing vigorous agitation, leading to homogenization of the samples. Air flows past and provides forced convection with a cold thermal mass, thereby reducing the temperature of the air, which then flows into the main chamber of the laboratory instrument, reducing the temperature of the samples and reagents. The cold air flows through a channel around the perimeter of the chamber. The cold air enters the chamber through multiple inlets. There are multiple holes in the walls of the chamber so that the cold air enters the chamber at multiple inlet ports, thereby providing more even cooling than if there were a single inlet port. As the hub rotates and the strikers travel through the chamber of the instrument, they drag air around, causing mixing of the air and encouraging greater convective heat transfer from the tubes to the air, thereby encouraging the contents of all the tubes to be at approximately the same temperature and to reach the target temperature relatively quickly. Feedback from temperature sensors in the instrument combined with information about the operating conditions are used to infer the temperature of the samples and reagents, adjusting the amount of cooling accordingly. While this invention could accurately control the temperature of the air in the sample chamber, its purpose is to accurately control the temperature of the samples which are thermally separated by one or more walls from the air in the chamber. This is accomplished by using the operational parameters of the entire instrument to determine the temperature control.

To accurately control the temperature of samples in the instrument, a temperature sensor provides feedback to an electronic circuit, which controls the cooling system using an algorithm. To compensate for thermal resistances and the thermal masses of the sample and sample container, a temperature sensor can be shielded from direct contact with the cooling air. Likewise, a heater placed near the temperature sensor can simulate any heating of the sample caused by the instrument.

The microprocessor or other controller of the cooling system employs algorithms to compensate for the operational parameters, including motor speed, heating due to friction and heat emanating from motors or other electromechanical components. Sensors, for example, an encoder, hall effect sensor, magnetic sensor monitoring the rotational speed of the motor, sensor monitoring the electrical power flowing through the motor, and/or an optical sensor with image processing monitoring the oscillations of the sample tubes, communicate information to the electronics circuit. The algorithm uses current information as well as past information to infer changes and rates of changes of the temperature, such as with PID control. The algorithm can also adjust the cooling parameters as a function of time, thereby taking into consideration the building up of heat and/or reactions occurring in the sample tubes.

The amount of cooling of the samples, i.e. the volume of air flowing past the cold thermal mass and then by the samples, is controlled by modulation of the speed of the fan. The internal volume of air can be recirculated in a loop past the components to be cooled and the cold thermal mass.

If the thermal mass is not in place, ambient air can still flow through the instrument, thereby removing any built-up heat.

In another embodiment, a blower is used in place of a fan.

In another embodiment, cooling is controlled by a proportional valve which adjusts the air flow past the cold thermal mass or past the samples. Likewise, a solenoid valve that is either open or closed, operating under pulse width or pulse period modulation, will modulate the volume of cold air entering the main chamber of the instrument, or alternatively, modulating the volume of cold air flowing past a cold thermal mass. Also, a multi-way valve can control the amount of cooling air introduced into the air flow circuit. Cooling can also be controlled by modulation of a cooling source, for example by changing the cold side temperature of a refrigeration unit by means of modulating the power supplied to the refrigeration unit.

Thermal cycling can be achieved with the following thermal management system. Using valves or a plurality of fans or blowers, air can alternately flow past two or more thermal masses or temperature sources. One of these thermal masses or thermal source would be relatively hot, and another relatively cold. By alternating which thermal mass the air flows past, the samples are thermal cycled.

Inputs to the temperature controller could come from sensors monitoring a sample. For example, a sensor could monitor a chemical reaction. The output from the sensor, perhaps an indication by change in the fluorescence or the absorbance of a sample, could determine the desired temperature of a sample or when cooling is or is not desired.

Analogously, this invention can also heat up samples. Heat pellets could be in the bucket or in an additional bucket to enable heating of the samples in the sample chamber.

In place of the bucket with cold pellets, a refrigeration coil or other refrigeration or chiller thermal transfer device could be used.

We claim:

1. A laboratory instrument for homogenizing samples, wherein said laboratory instrument oscillates said samples within sample holders by using a motor to rotate a hub with strikers that are positioned to impact said sample holders upon rotation, with temperature control of said samples, comprising:
   a. a chamber for storing a thermal mass;
   b. a thermal mass;
   c. a sample chamber;
   d. a means to provide forced convection with a flow of air by said thermal mass;
   e. a means for modulating said flow of air into said sample chamber;
   f. at least one temperature sensor;
   g. a motor speed sensor;
   h. an electronic circuit in communication with said at least one temperature sensor and with said motor speed sensor; and
   i. said electronic circuit providing a means for controlling the operation of the instrument; wherein said electronic circuit comprises a controller configured to control said motor and modulate said flow of air using feedback from said motor speed sensor and said at least one temperature sensor.

2. The laboratory instrument in claim 1, wherein said thermal mass includes dry ice.

3. The laboratory instrument in claim 1, wherein said means to force said flow of air includes a fan.

4. The laboratory instrument in claim 1, wherein said means to force said flow of air includes a blower.

5. The laboratory instrument in claim 1, wherein said means for modulating said flow of air includes a valve to throttle the flow.

6. The laboratory instrument in claim 1, wherein said means for modulating said flow of air includes a valve to redirect a portion of said flow of air.

7. The laboratory instrument in claim 1, wherein at least one said temperature sensor is shielded.

8. The laboratory instrument in claim 1, wherein said laboratory instrument oscillates biological samples for analysis.

9. The laboratory instrument in claim 1, wherein said laboratory instrument incubates samples with reagents.

10. A laboratory instrument of claim 1, with:
    a. a plurality of thermal chambers for storing thermal masses at different temperatures; and
    b. a means for alternating the flow of air past said thermal chambers to said sample chamber.

11. The laboratory instrument in claim 10, wherein said means for modulating air includes a valve.

12. A method of controlling the temperature of samples contained during homogenization in a laboratory instrument for homogenizing samples, wherein said laboratory instrument oscillates said samples within sample holders by using a motor to rotate a hub with strikers that are positioned to impact said sample holders upon rotation, comprising:
    a. providing forced convection with a flow of air by a thermal mass;
    b. receiving signals from at least one temperature sensor;
    c. controlling at least one electromechanical component for controlling a flow of air;

d. modulating said flow of air using an algorithm that uses said signals and that accounts for thermal effects resulting from the operation of said instrument;
e. receiving signals from a motor speed sensor; and
f. controlling the operation of said instrument and the temperature of said samples using an electronic circuit, wherein said electronic circuit comprises a controller configured to control said motor and modulate said flow of air using feedback from said motor speed sensor and said at least one temperature sensor.

13. The method in claim 12, wherein said modulating of air flow includes throttling of the flow of air.

14. The method in claim 12, wherein said modulating of air flow includes redirecting of a portion of the flow of air.

15. The method in claim 12, wherein said algorithm utilizes information of the operational parameters.

16. The laboratory instrument in claim 1, wherein said electronic circuit includes means to monitor the operating conditions of said oscillation.

17. The laboratory instrument in claim 1, wherein said laboratory instrument includes a sensor to monitor the operating conditions of said oscillation.

18. The method in claim 12, wherein said algorithm utilizes signals from a sensor that monitors the operating conditions of said laboratory instrument.

* * * * *